United States Patent
Mueller et al.

(10) Patent No.: US 7,244,821 B2
(45) Date of Patent: Jul. 17, 2007

(54) **USE OF *SACCHAROMYCES CEREVISIAE* ERG4 MUTANTS FOR EXPRESSING MAMMALIAN GLUCOSE TRANSPORTERS**

(75) Inventors: Guenter Mueller, Sulzbach am Taunus (DE); Silke Dlugai, Dusseldorf (DE); Doerthe Voss, Dusseldorf (DE); Eckhard Boles, Dusseldorf (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 355 days.

(21) Appl. No.: 10/659,234

(22) Filed: Sep. 10, 2003

(65) Prior Publication Data

US 2005/0074845 A1 Apr. 7, 2005

Related U.S. Application Data

(60) Provisional application No. 60/455,340, filed on Mar. 17, 2003.

(30) Foreign Application Priority Data

Sep. 14, 2002 (DE) ................. 102 42 763

(51) Int. Cl.
*C07K 1/00* (2006.01)
*C12P 21/06* (2006.01)
*C07H 21/04* (2006.01)
*C12N 1/12* (2006.01)

(52) U.S. Cl. .............. 530/350; 435/4; 435/6; 435/69.1; 435/252.3; 435/255; 435/255.1; 435/320.1; 536/23.4; 536/23.5; 536/23.6; 536/23.74

(58) Field of Classification Search ............ 435/4, 435/6, 69.1, 183, 252.3, 320.1, 254.1, 254.21, 435/255.2; 436/86, 87; 536/23.5; 530/350
See application file for complete search history.

(56) References Cited

U.S. PATENT DOCUMENTS

| | | |
|---|---|---|
| 6,346,374 B1 | 2/2002 | Tartaglia |
| 2004/0101848 A1* | 5/2004 | Ward et al. .............. 435/6 |
| 2005/0147987 A1* | 7/2005 | Venter et al. ............ 435/6 |

FOREIGN PATENT DOCUMENTS

| | | |
|---|---|---|
| WO | WO 00/75188 | 12/2000 |
| WO | WO 02/064784 | 8/2002 |

OTHER PUBLICATIONS

Fukumoto et al. (JBC, 1989, vol. 264(14):7776-7779 and Gen Bank Acc No. M20747, 1995).*
Burns Nancy et al., Large-Scale Analysis Of Gene Expression, Protein Localization, And Gene Disruption In *Saccharomyces cerevisiae*, Genes & Development, (1994), vol. 8, pp. 1087-1105.
Buse, John B. et al., Human GLUT4/Muscle-Fat Glucose-Transporter Gene, Diabetes, (1992), vol. 41, pp. 1436-1445.
Wieczorke Roman et al., Concurrent Knock-Out Of At Least 20 Transporter Genes Is Required To Block Uptake Of Hexoses In *Saccharomyces cerevisiae*, FEBS Letter, (1999), vol. 464, pp. 123-128.

* cited by examiner

Primary Examiner—Manjunath Rao

(57) ABSTRACT

The invention relates to yeast strains in which a human GLUT4 transport or a human GLUT1 transporter can be functionally expressed and to particular GLUT4 transport proteins which can be functionally expressed particularly readily in yeast strains.

25 Claims, No Drawings

USE OF *SACCHAROMYCES CEREVISIAE* ERG4 MUTANTS FOR EXPRESSING MAMMALIAN GLUCOSE TRANSPORTERS

PRIORITY CLAIM

This Application claims the benefit of U.S. Provisional Application No. 60/455,340 filed Mar. 17, 2003, and also claims priority from German Patent Application No. 10242763.1 filed Sep. 14, 2002.

FIELD OF THE INVENTION

The invention relates to yeast strains in which the human Glut 4 and Glut 1 transporters can be functionally expressed.

BACKGROUND OF THE INVENTION

Most heterotropic cells transport glucose via special transporter proteins into the cell interior. The various organisms have developed different mechanisms mediating the transporting of glucose, such as, in particular, proton symport systems, $Na^+$ glucose transporters, binding protein-dependent systems, phosphotransferase systems, and systems for facilitated diffusion. In the eukaryotes, a family of glucose transporters which are encoded in mammals by the GLUT genes (GLUT=glucose transporter) and *Saccharomyces cerevisiae* by the HXT genes (HXT=hexose transporter) mediates glucose uptake via facilitated diffusion. Said transporters belong to a larger family of sugar transporters. They are characterized by the presence of 12 transmembrane helices and by a plurality of conserved amino acid radicals. Glucose transport plays an important part in disorders associated with a defective glucose homeostasis, such as, for example, diabetes mellitus or Fanconi-Bickel syndrome. The glucose transport in mammals has therefore been the subject of numerous studies. To date, thirteen glucose transporter-like proteins have been identified (GLUT1 to GLUT12, HMIT—H-myo-inositol transporter)). Said transporters play key parts which include the uptake of glucose into various tissues, its storage in the liver, its insulin-dependent uptake into muscle cells and adipocytes and glucose measurement by the β cells of the pancreas.

GLUT1 mediates the transport of glucose into erythrocytes and through the blood-brain barrier, but is also expressed in many other tissues, while GLUT4 is limited to insulin-dependent tissues, primarily to muscle and fatty tissue. In said insulin-dependent tissues, controlling the targeting of GLUT4 transporters through intracellular compartments or plasma membrane compartments represents an important mechanism for regulating glucose uptake. In the presence of insulin, intracellular GLUT 4 is redistributed through the plasma membrane in order to facilitate glucose uptake. GLUT1 is likewise expressed in said insulin-dependent tissues, and its distribution in the cell is likewise influenced by insulin, albeit not as strongly. In addition, the relative efficacy with which GLUT1 or GLUT4 catalyze sugar transport is determined not only by the extent of the targeting of each transporter to the cell surface but also by their kinetic properties.

The fact that different glucose transporter isoforms are coexpressed and the rapid glucose metabolism have rendered studies on the role and the exact properties of each glucose transporter isoform in these insulin-dependent tissues complicated. In order to solve these problems, heterologous expression systems such as *Xenopus* oocytes, tissue culture cells, insect cells and yeast cells have been used. However, it turned out that a number of difficulties appeared in connection with these systems: too weak an activity of the heterologously expressed transporters, intrinsic glucose transporters in said systems, intracellular retention of a considerable proportion of the transporters or even production of inactive transporters.

Naturally occurring GLUT4 protein of mammals, in particular that of humans, can be expressed in a functional manner in strains of *Saccharomyces cerevisiae* under particular conditions.

Yeast cells are unicell eukaryotic organisms. They are therefore, for some proteins, more suitable for expression than bacterial systems, in particular with regard to carrying out screen assays for identifying pharmaceutically active substances.

The present invention relates to a purified and isolated polynucleotide comprising a DNA sequence which codes for the GLUT4V85M protein.

SUMMARY OF THE INVENTION

Said protein contains at position 85 of the amino acid chain of the human GLUT4 protein an amino acid exchange from valine to methionine. This altered GLUT4V85M protein provides further alternatives for expressing a functional GLUT4 protein. A GLUT4 protein should be regarded as functional in connection with *Saccharomyces cerevisiae* if glucose uptake can be observed in a *Saccharomyces cerevisiae* strain whose glucose transporters in their entirety are inactive (=hxt(−)) after expression of said GLUT4 protein. Glucose uptake may be determined either by transport measurements by means of radioactively labeled glucose or by growth on medium with glucose as sole carbon source.

In a preferred embodiment, the purified and isolated polynucleotide comprising a DNA sequence which calls for a protein GLUT4V85M may include or comprise a sequence of the following groups:
 a) a nucleotide sequence according to Seq ID No. 1,
 b) a nucleotide sequence which hybridizes to a sequence of Seq ID No. 1 under stringent conditions and which codes for a protein GLUT4V85M.

The purified and isolated polynucleotide preferably encodes a GLUT4V85M protein which has an amino acid sequence of Seq ID No. 2. The purified and isolated polynucleotide comprising a DNA sequence which codes as discussed previously for a protein GLUT4V85M, may be operationally linked to a promoter. Suitable promoters are in particular prokaryotic or eukaryotic promoters such as, for example, the Lac-, trp-, ADH- or HXT7 promoter. The part of the polynucleotides, which codes for the protein GLUT4V85M is operationally linked to a promoter so that a bacterial or eukaryotic organism can produce, by means of said promoter with the aid of a vector, an mRNA which can be translated into the protein GLUT4V85M. An example of such a vector is the vector p4H7GLUT4VS85M (Seq ID No. 3). The protein GLUT4V85M may be expressed in yeast cells by means of said vector.

The above-described polynucleotide comprising a DNA sequence which codes for a protein GLUT4V85M is, in a preferred embodiment, suitable for replicating said polynucleotide in a yeast cell or for expressing the part of the polynucleotide, which encodes the protein GLUT4V85M, in a yeast cell in order to produce GLUT4V85M protein. A yeast cell from *Saccharomyces cerevisiae* is particularly suitable. For replication and expression in a yeast cell, the polynucleotide comprising a DNA sequence which encodes GLUT4V85M protein is present in the form of a yeast vector. The polynucleotide region coding for the GLUT4V85M protein may be operationally linked to a yeast cell-specific promoter such as, for example, the ADH promoter (alcohol dehydrogenase promoter) or the HXT7 promoter (hexose-transporter promotor). The yeast sectors are a group of vectors which were developed for cloning DNA in yeasts.

The invention further extends to a *Saccharomyces cerevisiae* yeast cell in which all glucose transporters are no longer functional (=hxt(−)) and which contains no functional Erg4 protein. Such a yeast cell is preferably a yeast cell deposited as *Saccharomyces cerevisiae* DSM 15187 with the DSMZ (Deutsche Sammlung von Mikroorganismen und Zellkulturen GmbH, Mascheroder Weg 1b. D-38124 Braunschweig Germany), an International Depository Authority (IDA) as established under the Budapest Treaty on the International Recognition of the Deposit of Microorganisms for the Purposes of Patent Procedure, on Sep. 10, 2002.

The invention also extends to a yeast cell in which all glucose transporters are no longer functional and which contains no functional Fgy1 and no functional Erg4 protein. The lack of a functional Erg4 protein and a functional Fgy1 protein may be attributed in particular to an interruption of the corresponding coding genome sections or to a partial or complete removal of said coding genome sections. A particular example of a yeast cell of the present invention which contains no functional glucose transporters, no functional Fgy1 protein and no functional Erg4 protein, was deposited with the DSMZ as *Saccharomyces cerevisiae* DSM 15184 on Sep. 10, 2002. A yeast cell of the present invention has applications in the expression of a mammalian GLUT1 protein or a mammalian GLUT4 protein, particularly from rats, mice, rabbits, pigs, cattle or primates. A preferred embodiment uses a yeast cell of the present invention for expressing a human GLUT4 or GLUT1 protein.

A *Saccharomyces cerevisiae* yeast cell of the present invention whose glucose transporters in their entirety and also the Erg4 protein are no longer functional may contain a polynucleotide of the present invention that encodes a GLUT4V85M protein, that is operationally linked to a yeast-cell specific promoter. Naturally, such a yeast cell of the present invention can also express the GLUT4V85M protein, and thus contain said protein.

A particular example of a yeast cell of the present invention that contains a polynucleotide which encodes the GLUT4V85M protein and is operationally linked to a yeast-cell specific promoter, is preferably the *Saccharomyces cerevisiae* DSM 15185 yeast strain which was deposited with the DMSZ on Sep. 10, 2002.

Furthermore, the present invention extends to a method for producing a GLUT4V85M protein. Such a method comprises the steps of:
a) providing a yeast cell whose glucose transporters in their entirety are no longer functional and whose Erg4 protein is no longer functional,
b) providing an isolated and purified polynucleotide which comprises a DNA sequence coding for the GLUT4V85M protein and which can be replicated in the yeast cell,
c) transforming the yeast cell from a) with the polynucleotide from b),
d) selecting a transformed yeast cell,
e) where appropriate expressing the GLUT4V85M protein.

An isolated and purified polynucleotide which comprises a DNA sequence that encodes the GLUT4V85M protein is preferably contained within a vector which can be replicated in a yeast cell and in which said DNA sequence was cloned. An example of such a vector is p4H7GLUT4V85M (Seq ID No. 3).

The present invention also extends to a yeast cell whose glucose transporters in their entirety and whose proteins for Fgy1 and Erg4 are no longer functional and which contains a polynucleotide which comprises a DNA sequence coding for the GLUT4V85M protein operationally linked to a yeast-cell specific promoter. Said yeast cell can also express the GLUT4V85M protein and thus contain said protein. A yeast strain of this kind is preferably the *Saccharomyces cerevisiae* DSM 15186 deposited with the DSMZ on Sep. 10, 2002.

Naturally, the present invention extends to a method for producing the GLUT4V85M protein with a yeast cell of the present invention whose glucose transporters in their entirety and also whose Fgy1 and Erg4 are no longer functional, and which contains a polynucleotide comprising a DNA sequence which codes for the GLUT4V85M operationally linked to a yeast-cell specific promoter. Such a method comprises the steps of
a) providing a yeast cell whose glucose transporters in their entirety and also the proteins Fgy1 and Erg4 are no longer functional,
b) providing an isolated and purified polynucleotide which comprises a DNA sequence coding for the GLUT4V85M protein and which can be replicated in the yeast cell,
a) transforming the yeast cell from a) with the polynucleotide from b),
b) selecting a transformed yeast cell,
c) where appropriate expressing the GLUT4V85M protein.

The abovementioned isolated and purified polynucleotide which comprises a DNA sequence coding for the GLUT4V85M protein is preferably a vector which can be replicated in a yeast cell and in which said DNA sequence was cloned. An example of such a vector is p4H7GLUT4V85M (Seq ID No. 3).

The invention also relates to a yeast cell whose glucose transporters in their entirety are no longer functional and which contains a polynucleotide comprising a DNA sequence which calls for the GLUT4V85M protein. Said yeast cell can also express the GLUT4V85M protein and thus contain said protein. A preferred yeast strain of this kind is the *Saccharomyces cerevisiae* 15188 yeast strain deposited with the DSMZ.

A yeast cell whose glucose transporters in their entirety are no longer functional and which contains a polynucleotide comprising a DNA sequence which codes for the GLUT4 V85M protein may be prepared, for example, by
a) providing a yeast cell whose glucose transporters in their entirety are no longer functional,
b) providing an isolated and purified polynucleotide which comprises a DNA sequence coding for the GLUT4V85M protein and which can be replicated in the yeast cell,
c) transforming the yeast cell from a) with the polynucleotide from b),
d) selecting a transformed yeast cell,
e) where appropriate expressing the GLUT4V85M protein.

An isolated and purified polynucleotide which comprises a DNA sequence coding for the GLUT4V85M protein is preferably a vector which can be replicated in a yeast cell and in which said DNA sequence was cloned. An example of such a vector is p4H7GLUT4V85M (Seq ID No. 3).

The invention also relates to a protein having the amino acid sequence according to Seq ID No. 2. Said protein is a human GLUT4 protein in which a valine has been replaced by a methionine in position 85 of the amino acid chain.

The invention also relates to a method for identifying a compound which stimulates the activity of a GLUT4 protein, which method comprises the steps
a) providing a yeast cell whose glucose transporters in their entirety and also Erg4 protein are no longer functional and which contains a polynucleotide comprising a DNA sequence which codes for a protein GLUT4V85M,
b) providing a chemical compound,
c) contacting the yeast of a) with the chemical compound of b),
d) determining glucose uptake by the yeast of c),
e) relating the detected value of the glucose uptake of d) to the detected value of glucose uptake in a yeast cell as claimed in a) which has been contacted with a chemical compound as claimed in b), with a compound which causes an increase in the amount of glucose taken up in the yeast as claimed in d) stimulating the activity of said GLUT4 protein. Compounds which stimulate the activity of the GLUT4V85M protein can be assumed to stimulate also the GLUT4 activity.

The invention also relates to a pharmaceutical which contains a compound which has been identified by the method described above and furthermore to additives and excipients for formulating a pharmaceutical. Furthermore, the invention relates to the use of a compound which has been identified by the method described above for producing a pharmaceutical for the treatment of type I and/or II diabetes.

The invention also relates to a pharmaceutical comprising a compound which has been identified by the method described above and to additives and excipients for formulating a pharmaceutical. Furthermore, the invention relates to the use of a compound identified by the method described above for producing a pharmaceutical for the treatment of diabetes.

The invention furthermore relates to the use of a compound identified by a method described above for producing a pharmaceutical for the treatment of diabetes.

The present invention also comprises a method for identifying a compound which inhibits the protein encoded by the Erg4 gene, which method comprises the steps:
a) providing a yeast cell whose glucose transporters in their entirety and no longer functional and which contains a polynucleotide comprising a DNA sequence which codes for the GLUT4V85M protein and can be replicated in a yeast cell,
b) providing a chemical compound
c) contacting the yeast of a) with the chemical compound of b),
d) determining glucose uptake by the yeast of c),
e) relating the detected value of the glucose uptake of d) to the detected value of glucose uptake in a yeast cell as claimed in a) which is not contacted with a chemical compound as claimed in b), with a compound which causes an increase in the amount of glucose taken up in the yeast as claimed in d) stimulating the activity of a protein Erg4.

The invention furthermore relates to a method for identifying a compound inhibiting the corresponding protein of the Fgy1 gene, which comprises the steps:

a) providing a yeast cell whose glucose transporters in their entirety and whose Erg4 protein are no longer functional and which contains a GLUT4 protein,
b) providing a chemical compound
c) contacting the yeast of a) with the chemical compound of b),
d) determining glucose uptake by the yeast of c),
e) relating the detected value of the glucose uptake of d) to the detected value of glucose uptake in a yeast cell as claimed in a) which is not contacted with a chemical compound as claimed in b), with a compound which causes an increase in the amount of glucose taken up in the yeast as claimed in d) stimulating the activity of a protein Fgy1.

The invention also relates to a pharmaceutical comprising a compound which has been identified by the method described above and to additives and excipients for formulating a pharmaceutical.

The invention may be illustrated in more detail below with respect to technical details.

Hybridization means the assembling of two nucleic acid single strands having complementary base sequences to double strands. Hybridization may take place between two DNA strands, one DNA and one RNA strand and between two RNA strands. In principle, it is possible to prepare hybrid molecules by heating the nucleic acids involved which may initially be in double-stranded form, by boiling, for example, in a waterbath for 10 minutes, until they disintegrate into single-stranded molecules without secondary structure. Subsequently, they can be cooled slowly. During the cooling phase, complementary chains pair to give double-stranded hybrid molecules. Under laboratory conditions, hybridizations are usually carried out with the aid of hybridization filters to which single-stranded or denaturable polynucleotide molecules are applied by blotting or electrophoresis. It is possible to visualize the hybridization using appropriate complementary polynucleotide molecules by providing said polynucleotide molecules to be hybridized with a radioactive fluorescent label. Stringency describes the degree of matching or alignment of particular conditions. High stringency has higher demands on matching than low stringency. Depending on the application and objective, particular conditions with different stringency are set for the hybridization of nucleic acids. At high stringency, the reaction conditions for the hybridization are set in such a way that only complementary molecules which match very well can hybridize with one another. Low stringency enables molecules also to partially hybridize with relatively large sections of unpaired or mispaired bases.

The hybridization conditions are to be understood as being stringent, in particular, if the hybridization is carried out in an aqueous solution containing 2×SSC at 68° C. for at least 2 hours, followed by washing first in 2×SSC/0.1% SDS at room temperature for 5 minutes, then in 1×SSC/0.1% SDS at 68° C. for 1 hour and then in 0.2% SSC/0.1% SDS at 68° C. for another hour.

A 2×SSC, 1×SSC or 0.2×SSC solution is prepared by diluting a 20×SSC solution appropriately. A 20×SSC solution contains 3 mol/l NaCl and 0.3 mol/l Na citrate. The pH is 7.0. The skilled worker is familiar with the methods for hybridizations of polynucleotides under stringent conditions. Appropriate instructions can be found in specialist books such as, in particular, Current Protocols in Molecular Biology (Wiley Interscience; editors: Frederich M. Ausubel, Roger Brant, Robert E. Kingston, David J. Moore, J. G. Seidmann, Kevin Struhl; ISBN: 0-471-50338-X).

The yeast vectors can be divided into different subgroups. YIp vectors (yeast integrating plasmids) essentially correspond to the vectors used in bacteria for clonings, but contain a selectable yeast gene (e.g. URA3, LEU2).

Only when the foreign DNA integrates into a yeast chromosome after introduction of said vector, are these sequences replicated together with the chromosome and, with the formation of a clone, stably transferred to all daughter cells.

Based on this method, plasmids have been derived which can replicate autonomously owing to eukaryotic ORIs (origins of replication). Such yeast vectors are referred to as YRp vectors (yeast replicating plasmids) or ARS vectors (autonomously replicating sequence). Furthermore, there are YEp vectors (yeast episomal plasmids) which are derived from the yeast 2 μm plasmid and which contain a selective marker gene. The class of the YAC vectors (yeast artificial chromosome) behave like independent chromosomes.

A yeast vector containing a gene to be expressed is introduced into the yeast by means of transformation in order for said gene to be able to be expressed. Examples of methods suitable for this purpose are electroporation or incubation of competent cells with vector DNA. Suitable yeast expression promoters are known to the skilled worker, examples being the SOD1 promotor (superoxide dismutase), ADH promotor (alcohol dehydrogenase), the promotor of the gene for acidic phosphatase, HXT2 promotor (glucose transporter 2), HXT7 promotor (glucose transporter 7), GAL2 promotor (galactose transporter) and others. The construct comprising a yeast expression promotor and a gene to be expressed (e.g. GLUT4V85M) is, for the purpose of expression, part of a yeast vector. To carry out expression, said yeast vector may be a self-replicating particle which is independent of the yeast genome or may be stably integrated into the yeast genome. A suitable yeast vector is in principle any polynucleotide sequence which can be propagated in a yeast. Yeast vectors which may be used are in particular yeast plasmids or yeast artificial chromosomes. Yeast vectors usually contain an origin of replication (2μ, ars) or starting the replication process and a selection marker which usually comprises an auxotrophy marker or an antibiotic resistance gene. Examples of yeast vectors known to the skilled worker are pBM272, pCS19, pEMBCYe23, pFL26, pG6, pNN414, pTV3, p426MET25, p4H7 and others.

In accordance with the present invention, selection of a cell means the specific concentration thereof, owing to a selection marker such as, for example, resistance to an antibiotic or the ability to grow on a particular minimal medium, and furthermore the isolation and subsequent cultivation thereof on an agar plate or in submerged culture.

Cultivation, transformation and selection of a transformed yeast cell and also expression of a protein in a yeast cell are among the methods commonly used by the skilled worker. Instructions regarding said methods can be found in standard text books, for example in Walker Graeme M.: Yeast Physiology and Biotechnology, Wiley and Sons, ISBN: 0-471-9446-8 or in Protein Synthesis and Targeting in Yeast, Ed. Alistair J. P. Brown, Mick F. Fruite and John E. G. Mc Cartly; Springer Berlin; ISBN: 3-540-56521-3 or in "Methods in Yeast Genetics, 1997: A Cold Spring Harbor Laboratory Course Manual; Adams Alison (Edt.);. Cold Spring Harbor Laboratory; ISBN: 0-87969-508-0".

The yeast *Saccharomyces cerevisiae* has 17 known hexose transporters and additionally three known maltose transporters, which are capable of transporting hexoses into said yeast, provided that their expression is sufficiently high. In one known strain all transporters suitable for hexose uptake were removed by deletion. Said strain contains merely just the two genes MPH2 and MPH3 which are homologous to maltose transport proteins. The two genes MPH2 and MPH3 are repressed in the presence of glucose in the medium. Wieczorke et al., FEBS Lett. 464, 123–128 (1999) describe the preparation and characterization of this yeast strain. Said strain is not able to propagate on a substrate containing glucose as sole carbon source. It is possible to select from said strain mutants which functionally express GLUT1, starting from a corresponding vector (hxt fgy1-1 strain). If the yeast strain hxt fgy1-1 is transformed with a plasmid vector which carries a GLUT4 gene under control of a yeast promotor, still only very little glucose is transported. Functional GLUT4 expression requires further adjustments to this yeast strain in order to make possible a significant glucose transport by means of GLUT4. Such yeast strains whose cells take up glucose by means of a single glucose transporter GLUT4 can be isolated on substrates having glucose as sole carbon source. For this purpose, a yeast hxt fgy1-1 strain carrying a GLUT4 gene under the functional control of a yeast promotor is transformed. These yeast cells transformed in this way are applied to a nutrient medium containing glucose as sole carbon source and are incubated thereon. After a few days of incubation at, for example 30° C., the growth of individual colonies is observed. One of these colonies is isolated. The removal of the yeast plasmid from said colony prevents propagation on the nutrient medium containing glucose as sole carbon source. If this strain which no longer contains a vector plasmid is again transformed with a yeast vector carrying a GLUT4 gene under the functional control of a yeast promotor, said strain is then again able to propagate on a medium containing glucose as sole carbon source.

The abovementioned yeast strains are the subject matter of International Application PCT/EP02/01373, filed on Feb. 9, 2002, which claims the priority of DE 10106718.6 of Feb. 14, 2002.

Yeast strains whose indigenous transporters for hexoses (glucose transporters) in their entirety are no longer functional have already been deposited at an earlier date in connection with International Application PCT/EP02/01373 with the Deutsche Sammlung von Mikroorganismen und Zellkulturen GmbH (DSMZ) under the number DSM 14035, DSM 14036 or DSM 14037.

The polynucleotide and amino acid sequences of GLUT4 are accessible, for example, via the following entries in gene banks: M20747 (cDNA; human), EMBL: D28561 (cDNA; rat), EMBL: M23382 (cDNA; mouse), Swissprot: P14672 (protein; human), Swissprot: P19357 (protein; rat) and Swissprot: P14142 (protein; mouse).

Polynucleotide sequences and amino acid sequences of GLUT1 are disclosed under the following code numbers of the databases indicated: EMBL: M20653 (cDNA; human), EMBL: M13979 (cDNA; rat), EMBL: M23384 (cDNA; mouse), Swissprot: P11166 (protein; human), Swissprot: P11167 (protein; rat) and Swissprot: P17809 (protein; mouse).

Pharmaceuticals are dosage forms of pharmacologically active substances for the therapy of diseases or bodily malfunctions in humans and animals. Examples of dosage forms for oral therapy are powders, granules, tablets, pills, lozenges, sugar-coated tablets, capsules, liquid extracts, tinctures and syrups. Examples which are used for external application are aerosols, sprays, gels, ointments or powders. Injectable or infusible solutions allow parenteral administration, using vials, bottles or prefilled syringes. These and other pharmaceuticals are known to the skilled worker in the field of pharmaceutical technology.

Excipients for formulating a pharmaceutical made possible the preparation of the active substance with the purpose of optimizing the application, distribution and development of action of the active ingredient for the particular application. Examples of such excipients are fillers, binders, disintegrants or glidants, such as lactose, sucrose, mannitol, sorbitol, cellulose, starch, dicalcium phosphate, polyglycols, alginates, polyvinylpyrrolidone, carboxymethylcellulose, talc or silicon dioxide.

Diabetes manifests itself by the excretion of glucose together with the urine with an abnormal increase in the blood glucose level (hyperglycaemia), owing to a chronic metabolic condition due to insulin deficiency or reduced insulin action. The lack of, or reduced, insulin action leads to insufficient absorption and conversion by the cells of the glucose taken up into the blood. In fatty tissue, insulin-antagonistic hormones have the effect of increasing lypolysis accompanied by an increase in the free fatty acid levels in the blood.

Adiposity (obesity) is the abnormal weight gain owing to an energy imbalance due to excessive intake of calories, which constitutes a health risk.

The amount of a hexose which is taken up by a provided yeast strain as described just above can be determined by means of uptake studies using radioactively labeled glucose. For this purpose, a particular amount of the yeast cells is suspended in, for example, 100 µl of a buffer, for example at a concentration of 60 mg (wet weight) per ml, and admixed with a defined amount of $^{14}C$- or $^{3}H$-labeled glucose as sole carbon source. The cells are incubated, and defined amounts thereof are removed at specific times. The amount of glucose taken up is determined with the aid of LSC (Liquid Scintillation Counting). The amount of a hexose which is taken up by a yeast strain provided and as just described above may, however, also be determined by means of a growth assay on media containing glucose as sole carbon source. For this purpose, the rate of growth of the strain is determined, after addition of the compound, for example by measuring the optical density of the culture at 600 nm at regular intervals, and this value is compared with the rate of growth of a control strain (e.g. yeast wild-type strain).

A compound is provided, in particular, by chemical synthesis or by isolating chemical substances from biological organisms. It is also possible to carry out chemical synthesis in an automated manner. The compounds obtained by synthesis or isolation can be dissolved in a suitable solvent. Suitable solvents are in particular aqueous solutions which contain a specific proportion of an organic solvent such as, for example, DMSO (dimethylsulfoxide).

Conducting a strain of the yeast with a compound for identifying a compound in accordance with an invention mentioned above is done in particular in automated laboratory systems provided therefor. Such systems may comprise specifically prepared chambers with depressions, or microtiter plates, Eppendorf tubes or laboratory glassware. Automated laboratory systems are usually designed for high throughput rates. A method such as the one mentioned above, carried out with the aid of an automated laboratory system, is therefore also referred to as HTS (High Throughput Screening).

Seq ID No. 1 discloses a polynucleotide sequence comprising the coding region of the GLUT4V85M protein. Seq ID No. 2 discloses the amino acid sequence of the GLUT4V85M protein. Seq ID No. 3 discloses the polynucleotide sequence of the p4H7GLUT4V85M vector.

EXAMPLES

Use of Yeast Strains

All of the yeast strains described herein were derived from strain CEN-PK2-1C (MA Ta leu2-3, 112 ura3-52 trp 1-289 his3-Δ1MAL2-8$^c$ SUC2). The preparation of a yeast strain having deletions in the hexose transporter genes (HXT) has been described by Wieczorke et al., FEBS Lett. 464, 123–128 (1999): EBY-18ga (MATa Δhxt1-17 Δgal2 Δagt1 Δstl1 leu2-3, 112 ura3-52 trp1-289 his3-Δ1 MAL2-8$^c$ SUC2), EBY.VW4000 (MATa Δhxt1-17 Δgal2 Δagt1 Δmph2 Δmph3 Δstl1 leu2-3, 112 ura3-52 trp1-289 his3-Δ1 MAL2-8$^c$ SUC2). The media were based on 1% yeast extract and 2% peptone (YP), while the minimal media were composed of 0.67% Difco yeast nitrogen base without amino acids (YNB) and contained additives required for auxotrophy and different carbon sources. The yeast cells were grown under aerobic conditions at 30° C. on a rotary shaker or on agar plates. Cell growth was monitored by measuring the optical density at 600 nm ($OD_{600}$) or by determining the diameter of yeast colonies.

Determination of Glucose Uptake

Glucose transport was measured as uptake of D-[U-$^{14}$C]-glucoses (Amersham) and the kinetic parameters were determined from Eadie-Hofstee plots. The cells were removed by centrifugation, washed with phosphate-buffer and resuspended in phosphate buffer at a concentration of 60 mg (wet weight) per ml. Glucose uptake was determined for glucose concentrations between 0.2 and 100 mM, and the specific activity of the substrate was between 0.1 and 55.5 kBq µmol$^{-1}$. The cells and the glucose solutions were preincubated at 30° C. for 5 minutes. Glucose uptake was started by adding radioactive glucose to the cells. After incubation for 5 seconds, 10 ml of ice-cold stop buffer (0.1 M KiPO$_4$, pH 6.5, 500 mM glucose) were added and the cells were removed quickly by filtering on glass fiber filters (Ø=24 mm, Whatman). The filters were quickly washed three times with ice-cold buffer and the radioactivity incorporated was measured using a liquid scintillation counter. An addition by cytochalasin B (final concentration 20 µM, dissolved in ethanol) was measured in a 15-second uptake assay with 50 mM or 100 mM radioactive glucose, after the cells had been incubated in the presence of the inhibitor or of only the solvent for 15 minutes.

A novel heterologous expression system for glucose transporters from mammalian cells has been developed. The system is based on an *S. cerevisiae* strain from which all endogenous glucose transporters have been removed destroying the encoding genes. Said strain is no longer able to take up glucose via the plasma membrane and to grow with glucose as sole carbon source. In order to integrate the heterologous glucose transporters of humans or of other mammals, GLUT1 and GLUT4 in an active form into the yeast plasma membrane, additional mutations had to be introduced into the yeast strain. GLUT1 is active only in an fgy1-1 mutant strain and GLUT4 only in fgy1-1 fgy4-X double mutants.

The FGY1 gene has been cloned. It is the *S. cerevisiae* ORF YMR212c. With respect to the function, the results indicate that either Fgy1 or a product generated by Fgy1 inhibits the activity of human glucose transporters or is involved in fusing the GLUT-transporting vesicles to the plasma membrane.

In contrast to GLUT1 and similarly to mammalian cells, a large proportion of the GLUT4 proteins in the yeast is located in intracellular structures. A total of nine recessive mutants were isolated (fgy4-1 to fgy4-9) in which GLUT4 is now directed further to the plasma membrane and, in the case of a concomitant fgy1-1 mutation, becomes active there.

The insertion gene bank described by Bruns et al. (Genes Dev. 1994; 8: 1087–105) was used for complementation analysis. The hxt fgy1-1 strain was transformed first with a GLUT4 plasmid and then with the mobilized insertion gene bank. This was followed by screening for transformants which were able to grow on glucose medium. It turned out that in one of the mutants studied the ERG4 gene had been destroyed. ERG4 codes for an enzyme (oxidoreductase) of ergosterol biosynthesis. This enzyme, sterol C-24(28)-reductase catalyzes the last step of ergosterolbiosynthesis and converts ergosta-5,7,22,24,(28)-tetraenol to the final product ergosterol. The Erg4 protein presently contains eight transmembrane domains and is located in the endoplasmic reticulum. An erg4 mutant is viable, since incorporation of the ergosterol precursors into the yeast membranes compensates for the loss of ergosterol.

The inhibiting influence of Erg4 on GLUT4 functionality was confirmed by specific deletion of erg4 in the hxt fgy1-1 strain. The resulting strain (hxt fgy1-1 Δerg4) was referred to as SDY022.

Protein interaction assays with the aid of the split-ubiquitin system showed that human GLUT4 directly interacts with yeast Erg4. It can therefore be assumed that the yeast Erg4 protein in the endoplasmic reticulum either directly prevents further translocation of GLUT4 or modifies GLUT4 in some way which is important for translocation and/or function.

Likewise, it was shown that deletion of ERG4 in the hxt null strain alone, i.e. despite functional FGY1, activates GLUT1, but not GLUT4. The results of the growth assay are summarized in Table 1.

In order to rule out that Ergosterol itself exerts a negative influence on GLUT4, growth assays were carried out on agar plates containing Ergosterol under aerobic conditions. Any yeast strains transformed with GLUT4 were unable to grow under these conditions (Table 2). The GLUT1 transformants in the hxt fgy1-1 strain showed, in contrast to aerobic growth, no growth on glucose under anaerobic conditions. GLUT1 transformants were able to grow only after deletion of ERG4.

The exchange of Val85 for Met by in vitro mutagenesis rendered GLUT4 independent of the fgy1-1 mutation and resulted in GLUT4V85M being functional even in an hxt erg4 strain. This observation indicates that Fgy1 acts directly or indirectly on this position which is located within the second transmembrane helix of GLUT transporters.

Table 3 displays the descriptions of the yeast strains deposited in connection with the present patent application with the Deutsche Sammlung von Mikroorganismen und Zellkulturen (DSMZ)—MascheroderWeg 1b 38124 Brunswick, Germany.

TABLE 1

Growth of GLUT1 and GLUT4 transformants on glucose medium.

| Genotype | 1% Glucose | | 1% Glucose | |
| --- | --- | --- | --- | --- |
| Δhxt fgy1-1 | GLUT4 | − | GLUT1 | ++ |
| Δhxt fgy1-1 Δerg4 | GLUT4 | ++ | GLUT1 | ++ |
| Δhxt fgy1-1 Δerg4 | Vector | − | Vector | − |
| Δhxt fgy1-1 Δerg5 | GLUT4 | − | GLUT1 | ++ |
| Δhxt fgy1-1 Δerg4 Δerg5 | GLUT4 | + | GLUT1 | ++ |
| Δhxt Δerg4 | GLUT4 | − | GLUT1 | + |
| Δhxt Δerg5 | GLUT4 | − | GLUT1 | − |

TABLE 2

Growth of GLUT1 and GLUT4 transformants on glucose medium with or without ergosterol under anaerobic conditions

| Genotype | | 1% Glucose | 1% Glucose + 33 mg/l Ergosterol |
| --- | --- | --- | --- |
| Δhxt fgy1-1 | GLUT1 | − | − |
| | GLUT4 | − | − |
| Δhxt fgy1-1 Δerg4 | GLUT1 | − | ++ |
| | GLUT4 | − | − |
| Δhxt fgy1-1 Δerg5 | GLUT1 | − | − |
| | GLUT4 | − | − |
| Δhxt fgy1-1 Δerg4 Δerg5 | GLUT1 | − | ++ |
| | GLUT4 | − | − |
| Δhxt Δerg4 | GLUT1 | − | (+) |
| | GLUT4 | − | − |
| Δhxt Δerg5 | GLUT1 | − | − |
| | GLUT4 | − | − |

TABLE 3

Features of the deposited yeast strains (*Saccharomyces cerevisiae*)

| Number of deposit with the DSMZ | Genotype | Phenotype | Plasmid |
| --- | --- | --- | --- |
| DSM 15187 | MATa Δhxt1-17 Δgal2 Δagt1 Δstl1 Δmph2 Δmph3 Δerg4 leu2-3, 112 ura3-52 trp1-289 his3-Δ1 MAL2-8$^C$ SUC2 | Strain growth with 1% maltose as carbon source; auxotrophic for glucose, leucine, tryptophan, histidine and uracil | — |

TABLE 3-continued

Features of the deposited yeast strains (*Saccharomyces cerevisiae*)

| Number of deposit with the DSMZ | Genotype | Phenotype | Plasmid |
|---|---|---|---|
| DSM 15184 | MATa Δhxt1-17 Δgal2 Δagt1 Δstl1 Δerg4 fgy1-1 leu2-3, 112 ura3-52 trp1-289 his3-Δ1 MAL2-8$^C$ SUC2 | Strain growth with 1% maltose as carbon source; auxotrophic for glucose, leucine, tryptophan, histidine and uracil | — |
| DSM 15185 | MATa Δhxt1-17 Δgal2 Δagt1 Δstl1 Δmph2 Δmph3 Δerg4 leu2-3, 112 ura3-52 trp1-289 his3-Δ1 MAL2-8$^C$ SUC2 | Strain growth with 1% maltose as carbon source; auxotrophic for glucose, leucine, tryptophan and histidine | p4H7GLUT4V85M (Selection marker URA3), = Seq ID No. 3 |
| DSM 15186 | MATa Δhxt1-17 Δgal2 Δagt1 Δstl1 Δerg4 fgy1-1 leu2-3, 112 ura3-52 trp1-289 his3-Δ1 MAL2-8$^C$ SUC2 | Strain growth with 1% maltose as carbon source; auxotrophic for glucose, leucine, tryptophan and histidine | p4H7GLUT4V85M (Selection marker URA3) = Seq ID No. 3 |
| DSM 15188 | MATa Δhxt1-17 Δgal2 Δagt1 Δstl1 Δmph2 Δmph3 leu2-3, 112 ura3-52 trp1-289 his3-Δ1 MAL2-8$^C$ SUC2 | Strain growth with 1% maltose as carbon source; auxotrophic for glucose, leucine, tryptophan and histidine | p4H7GLUT4V85M (Selection marker URA3) = Seq ID No. 3 |

Basic medium: 0.67% Yeast Nitrogen Base without amino acids (Difco); pH 6.2. Auxotrophy supplementation: Leucine (0.44 mM), tryptophan (0.19 mM), histidine (0.25 mM9, uracil (0.44 mM). Maltose may be between 1–2%.

The invention claimed is:

1. The purified and isolated polynucleotide which comprises a DNA sequence coding for a glucose transporter 4 protein (GLUT4V85M) with valine at position 85 substituted with methionine, wherein said DNA sequence comprises the nucleotide sequence of SEQ ID NO:1.

2. The purified and isolated polynucleotide as claimed in claim 1, wherein the protein GLUT4V85M comprises the amino acid sequence of SEQ ID NO. 2.

3. The purified and isolated polynucleotide as claimed in claim 1, wherein the DNA sequence encoding the GLUT4V85M protein is operationally linked to a promoter.

4. The purified and isolated polynucleotide as claimed in claim 1 wherein said DNA sequence comprises a nucleotide sequence that hybridizes under stringent conditions to the nucleotide sequence of SEQ ID NO:1.

5. An expression vector comprising the purified and isolated polynucleotide of claim 3.

6. An isolated *Saccharomyces cerevisiae* yeast cell in which all glucose transporters are no longer functional, and which contains no functional Erg4 protein, wherein said yeast cell is transformed with the expression vector of claim 3.

7. The transformed yeast cell of claim 6, deposited as DSM15185.

8. The transformed yeast cell as claimed in claim 6, further lacking functional Fgy1 protein.

9. The transformed *Saccharomyces cerevisiae* yeast cell of claim 8, deposited as DSM15186.

10. A process of preparing an isolated *Saccharomyces cerevisiae* yeast cell which (i) expresses a GLUT4V85M protein comprising the amino acid sequence of SEQ ID NO:2, (ii) does not contain a functional glucose transporter, and (iii) lacks functional Erg4 protein, the process comprising the steps of
 a) providing a yeast cell from *Saccharomyces cerevisiae*, wherein all glucose transporters are no longer functional and which contains no functional Erg4 protein,
 b) providing an expression vector that comprises the nucleotide sequence of SEQ ID NO:1 operationally linked with a promoter and
 c) transforming the yeast cell of a) with the expression vector of b).

11. The isolated polynucleotide of claim 4, wherein the DNA sequence that encodes the GLUT4V85M protein is operationally linked to a promoter.

12. An expression vector comprising the isolated polynucleotide of claim 3.

13. An expression vector comprising the isolated polynucleotide of claim 11.

14. A process of preparing a *Saccharomyces cerevisiae* yeast cell which (i) expresses a GLUT4V85M protein comprising the amino acid sequence of SEQ ID NO:2, (ii) does not contain a functional glucose transporter, (iii) lacks functional Erg4 protein, and (iv) lacks functional Fgy1 protein, the process comprising the steps of:
 a) providing a yeast cell from *Saccharomyces cerevisiae*, wherein all glucose transporters are no longer functional, which contains no functional Erg4 protein, and which contains no functional Fgy1 protein, and
 b) providing an expression vector that comprises the nucleotide sequence of SEQ ID NO:1 operationally linked with a promoter and transforming the yeast cell of step (a) with the expression vector of step (b).

15. A *Saccharomyces cerevisiae* yeast cell whose glucose transporters in their entirety are no longer functional, transformed with the expression vector of claim 5.

16. The yeast cell as claimed in claim 15, wherein said DNA sequence of said expression vector comprises the nucleotide sequence of SEQ ID NO:1, and said GLUT4V85M protein comprises the amino acid sequence of SEQ ID NO:2.

17. The yeast cell as claimed in claim 16, deposited as *Saccharomyces cerevisiae* DSM 15188.

18. A process of preparing *Saccharomyces cerevisiae* yeast cell as claimed in claim 15 which comprises the steps:
 a) producing a *Saccharomyces cerevisiae* yeast cell whose glucose transporters in their entirety are no longer functional,
 b) providing an expression vector that comprises a purified and isolated polynucleotide comprising a DNA sequence that encodes a GLUT4V85M protein of SEQ ID NO:2.
 c) transforming the yeast cell of step (a) with the expression vector of step (b).

19. An isolated polynucleotide that encodes a polypeptide comprising the amino acid sequence of SEQ ID NO:2.

20. The isolated polynucleotide of claim 19, comprising the DNA sequence of SEQ ID NO:1.

21. An expression vector comprising the isolated polynucleotide of claim 2.

22. A *Saccharomyces cerevisiae* yeast cell whose glucose transporters in their entirety are no longer functional, transformed with the expression vector of claim 21.

23. The transformed yeast cell of claim 22, which lacks functional Erg4 protein.

24. The transformed yeast cell of claim 22, which lacks functional Fgy4 protein.

25. The transformed *Saccharomyces cerevisiae* yeast cell of claim 24, as deposited as *Saccharomyces cerevisiae* DSM 15186.

* * * * *

```
                        SEQUENCE LISTING

<160> NUMBER OF SEQ ID NOS: 3

<210> SEQ ID NO 1
<211> LENGTH: 1530
<212> TYPE: DNA
<213> ORGANISM: Homo sapiens

<400> SEQUENCE: 1
atgccgtcgg gcttccaaca gataggctcc gaagatgggg aaccccctca gcagcgagtg      60
actgggaccc tggtccttgc tgtgttctct gcggtgcttg ctccctgca gtttgggtac     120 aacattgggg tcatcaatgc ccctcagaag gtgattgaac agagctacaa tgagacgtgg     180
ctggggaggc aggggcctga gggacccagc tccatccctc aggcaccct caccaccctc     240 tgggccctct ccatggccat cttttccgtg ggcggcatga tttcctcctt cctcattggt     300
atcatctctc agtggcttgg aaggaaaagg gccatgctgg tcaacaatgt cctgcggtg     360 ctgggggca gcctcatggg cctggccaac gctgctgcct cctatgaaat gctcatcctt     420
ggacgattcc tcattggcgc ctactcaggg ctgacatcag gctggtgcc catgtacgtg     480 ggggagattg ctcccactca cctgcgggc gccctgggga cgctcaacca actggccatt     540
gttatcggca ttctgatcgc ccaggtgctg ggcttggagt ccctcctggg cactgccagc     600
ctgtggccac tgctcctggg cctcacagtg ctacctgccc tcctgcagct ggtcctgctg     660
cccttctgtc ccgagagccc ccgctacctc tacatcatcc agaatctcga ggggcctgcc     720
```

-continued

```
agaaagagtc tgaagcgcct gacaggctgg gccgatgttt ctggagtgct ggctgagctg      780
aaggatgaga agcggaagct ggagcgtgag cggccactgt ccctgctcca gctcctgggc      840
agccgtaccc accggcagcc cctgatcatt gcggtcgtgc tgcagctgag ccagcagctc      900
tctggcatca atgctgtttt ctattattcg accagcatct tcgagacagc agggtaggc       960 cagcctgcct atgccaccat aggagctggt gtggtcaaca cagtcttcac cttggtctcg     1020
gtgttgttgg tggagcgggc ggggcgccgg acgctccatc tcctgggcct ggcgggcatg     1080
tgtggctgtg ccatcctgat gactgtggct ctgctcctgc tggagcgagt tccagccatg     1140
agctacgtct ccattgtggc catctttggc ttcgtggcat tttttgagat tggccctggc     1200
cccattcctt ggttcatcgt ggccgagctc ttcagccagg accccgcccg gcagccatg      1260 gctgtggctg tttctccaa ctggacgagc aacttcatca ttggcatggg tttccagtat      1320
gttgcggagg ctatggggcc ctacgtcttc cttctatttg cggtcctcct gctgggcttc     1380
ttcatcttca ccttcttaag agtacctgaa actcgaggcc ggacgtttga ccagatctca     1440
gctgccttcc accggacacc ctctctttta gagcaggagg tgaaacccag cacagaactt     1500
gagtatttag gccagatga gaacgactga                                        1530
```

<210> SEQ ID NO 2
<211> LENGTH: 509
<212> TYPE: PRT
<213> ORGANISM: Homo sapiens

<400> SEQUENCE: 2

```
Met Pro Ser Gly Phe Gln Gln Ile Gly Ser Glu Asp Gly Glu Pro Pro
1               5                   10                  15

Gln Gln Arg Val Thr Gly Thr Leu Val Leu Ala Val Phe Ser Ala Val
            20                  25                  30

Leu Gly Ser Leu Gln Phe Gly Tyr Asn Ile Gly Val Ile Asn Ala Pro
        35                  40                  45

Gln Lys Val Ile Glu Gln Ser Tyr Asn Glu Thr Trp Leu Gly Arg Gln
    50                  55                  60

Gly Pro Glu Gly Pro Ser Ser Ile Pro Pro Gly Thr Leu Thr Thr Leu
65                  70                  75                  80

Trp Ala Leu Ser Met Ala Ile Phe Ser Val Gly Gly Met Ile Ser Ser
                85                  90                  95

Phe Leu Ile Gly Ile Ile Ser Gln Trp Leu Gly Arg Lys Arg Ala Met
            100                 105                 110

Leu Val Asn Asn Val Leu Ala Val Leu Gly Gly Ser Leu Met Gly Leu
        115                 120                 125

Ala Asn Ala Ala Ala Ser Tyr Glu Met Leu Ile Leu Gly Arg Phe Leu
    130                 135                 140

Ile Gly Ala Tyr Ser Gly Leu Thr Ser Gly Leu Val Pro Met Tyr Val
145                 150                 155                 160

Gly Glu Ile Ala Pro Thr His Leu Arg Gly Ala Leu Gly Thr Leu Asn
                165                 170                 175

Gln Leu Ala Ile Val Gly Ile Leu Ile Ala Gln Val Leu Gly Leu
            180                 185                 190

Glu Ser Leu Leu Gly Thr Ala Ser Leu Trp Pro Leu Leu Gly Leu
        195                 200                 205

Thr Val Leu Pro Ala Leu Leu Gln Leu Val Leu Pro Phe Cys Pro
    210                 215                 220

Glu Ser Pro Arg Tyr Leu Tyr Ile Ile Gln Asn Leu Glu Gly Pro Ala
```

-continued

```
             225                 230                 235                 240
    Arg Lys Ser Leu Lys Arg Leu Thr Gly Trp Ala Asp Val Ser Gly Val
                    245                 250                 255
    Leu Ala Glu Leu Lys Asp Glu Lys Arg Lys Leu Glu Arg Glu Arg Pro
                260                 265                 270
    Leu Ser Leu Leu Gln Leu Gly Ser Arg Thr His Arg Gln Pro Leu
            275                 280                 285
    Ile Ile Ala Val Val Leu Gln Leu Ser Gln Gln Leu Ser Gly Ile Asn
        290                 295                 300
    Ala Val Phe Tyr Tyr Ser Thr Ser Ile Phe Glu Thr Ala Gly Val Gly
    305                 310                 315                 320
    Gln Pro Ala Tyr Ala Thr Ile Gly Ala Gly Val Val Asn Thr Val Phe
                    325                 330                 335
    Thr Leu Val Ser Val Leu Leu Val Glu Arg Ala Gly Arg Arg Thr Leu
                340                 345                 350
    His Leu Gly Leu Ala Gly Met Cys Gly Cys Ala Ile Leu Met Thr
            355                 360                 365
    Val Ala Leu Leu Leu Leu Glu Arg Val Pro Ala Met Ser Tyr Val Ser
    370                 375                 380
    Ile Val Ala Ile Phe Gly Phe Val Ala Phe Glu Ile Gly Pro Gly
    385                 390                 395                 400
    Pro Ile Pro Trp Phe Ile Val Ala Glu Leu Phe Ser Gln Gly Pro Arg
                    405                 410                 415
    Pro Ala Ala Met Ala Val Ala Gly Phe Ser Asn Trp Thr Ser Asn Phe
                420                 425                 430
    Ile Ile Gly Met Gly Phe Gln Tyr Val Ala Glu Ala Met Gly Pro Tyr
            435                 440                 445
    Val Phe Leu Leu Phe Ala Val Leu Leu Gly Phe Phe Ile Phe Thr
    450                 455                 460
    Phe Leu Arg Val Pro Glu Thr Arg Gly Arg Thr Phe Asp Gln Ile Ser
    465                 470                 475                 480
    Ala Ala Phe His Arg Thr Pro Ser Leu Leu Glu Gln Glu Val Lys Pro
                    485                 490                 495
    Ser Thr Glu Leu Glu Tyr Leu Gly Pro Asp Glu Asn Asp
                500                 505
```

<210> SEQ ID NO 3
<211> LENGTH: 7809
<212> TYPE: DNA
<213> ORGANISM: Saccharomyces cerevisiae

<400> SEQUENCE: 3

```
cgtaggaaca atttcgggcc cctgcgtgtt cttctgaggt tcatctttta catttgcttc      60
tgctggataa ttttcagagg caacaaggaa aaattagatg gcaaaaagtc gtctttcaag     120
gaaaaatccc caccatcttt cgagatcccc tgtaacttat tggcaactga agaatgaaa      180
aggaggaaaa tacaaaatat actagaactg aaaaaaaaaa agtataaata gagacgatat     240
atgccaatac ttcacaatgt tcgaatctat tcttcatttg cagctattgt aaaataataa     300
aacatcaaga acaacaaagc tcaacttgtc ttttctaaga acaagaata acacaaaaa      360
caaaaagttt ttttaatttt aatcaaaaaa tgccgtcggg cttccaacag ataggctccg     420
aagatgggga acccctcag cagcgagtga ctgggaccct ggtccttgct gtgttctctg     480
cggtgcttgg ctccctgcag tttgggtaca acattgggt catcaatgcc cctcagaagg     540
```

-continued

```
tgattgaaca gagctacaat gagacgtggc tggggaggca ggggcctgag ggacccagct       600
ccatccctcc aggcaccctc accaccctct gggccctctc catggccatc ttttccgtgg       660
gcggcatgat ttcctccttc ctcattggta tcatctctca gtggcttgga aggaaaaggg       720
ccatgctggt caacaatgtc ctggcggtgc tgggggcag cctcatgggc ctggccaacg        780
ctgctgcctc ctatgaaatg ctcatccttg acgattcct cattggcgcc tactcagggc        840
tgacatcagg gctggtgccc atgtacgtgg gggagattgc tcccactcac ctgcggggcg       900
ccctggggac gctcaaccaa ctggccattg ttatcggcat tctgatcgcc caggtgctgg       960
gcttggagtc cctcctgggc actgccagcc tgtggccact gctcctgggc ctcacagtgc      1020
tacctgccct cctgcagctg gtcctgctgc ccttctgtcc cgagagcccc cgctacctct      1080
acatcatcca gaatctcgag gggcctgcca gaaagagtct gaagcgcctg acaggctggg      1140
ccgatgtttc tggagtgctg gctgagctga aggatgagaa gcggaagctg gagcgtgagc      1200
ggccactgtc cctgctccag ctcctgggca gccgtaccca ccggcagccc ctgatcattg      1260
cggtcgtgct gcagctgagc cagcagctct ctggcatcaa tgctgttttc tattattcga      1320
ccagcatctt cgagacagca ggggtaggcc agcctgccta tgccaccata ggagctggtg      1380
tggtcaacac agtcttcacc ttggtctcgg tgttgttggt ggagcgggcg gggcgccgga      1440
cgctccatct cctgggcctg gcgggcatgt gtggctgtgc catcctgatg actgtggctc      1500
tgctcctgct ggagcgagtt ccagccatga gctacgtctc cattgtggcc atctttggct      1560
tcgtggcatt ttttgagatt ggccctggcc ccattccttg gttcatcgtg gccgagctct      1620
tcagccaggg accccgcccg gcagccatgg ctgtggctgg tttctccaac tggacgagca      1680
acttcatcat tggcatgggt ttccagtatg ttgcggaggc tatggggccc tacgtcttcc      1740
ttctatttgc ggtcctcctg ctgggcttct tcatcttcac cttcttaaga gtacctgaaa      1800
ctcgaggccg gacgtttgac cagatctcag ctgccttcca ccggacaccc tctcttttag      1860
agcaggaggt gaaacccagc acagaacttg agtatttagg gccagatgag aacgactgac      1920
tcgagtcatg taattagtta tgtcacgctt acattcacgc cctcccccca catccgctct      1980
aaccgaaaag gaaggagtta gacaacctga agtctaggtc cctatttatt tttttatagt      2040
tatgttagta ttaagaacgt tatttatatt tcaaattttt ctttttttc tgtacagacg       2100
cgtgtacgca tgtaacatta tactgaaaac cttgcttgag aaggttttgg gacgctcgaa      2160
ggctttaatt tgcggccggt acccaattcg ccctatagtg agtcgtatta cgcgcgctca      2220
ctggccgtcg ttttacaacg tcgtgactgg gaaaaccctg gcgttaccca acttaatcgc      2280
cttgcagcac atccccvttt cgccagctgg cgtaatagcg aagaggcccg caccgatcgc      2340
ccttcccaac agttgcgcag cctgaatggc gaatggcgcg acgcgccctg tagcggcgca      2400
ttaagcgcgg cgggtgtggt ggttacgcgc agcgtgaccg ctacacttgc cagcgcccta      2460
gcgcccgctc ctttcgcttt cttcccttcc tttctcgcca cgttcgccgg ctttccccgt      2520
caagctctaa atcgggggct ccctttaggg ttccgattta gtgctttacg cacctcgac       2580
cccaaaaaac ttgattaggg tgatggttca cgtagtgggc catcgccctg atagacggtt      2640
tttcgccctt tgacgttgga gtccacgttc tttaatagtg gactcttgtt ccaaactgga      2700
acaacactca accctatctc ggtctattct tttgatttat aagggatttt gccgatttcg      2760
gcctattggt taaaaaatga gctgatttaa caaaaattta cgcgaatttt aacaaaata      2820
ttaacgtttta caatttcctg atgcggtatt ttctccttac gcatctgtgc ggtatttcac      2880
accgcatagg gtaataactg atataattaa attgaagctc taatttgtga gtttagtata      2940
```

-continued

| | |
|---|---|
| catgcattta cttataatac agttttttag ttttgctggc cgcatcttct caaatatgct | 3000 |
| tcccagcctg cttttctgta acgttcaccc tctaccttag catcccttcc ctttgcaaat | 3060 |
| agtcctcttc caacaataat aatgtcagat cctgtagaga ccacatcatc cacggttcta | 3120 |
| tactgttgac ccaatgcgtc tcccttgtca tctaaaccca caccgggtgt cataatcaac | 3180 |
| caatcgtaac cttcatctct tccacccatg tctctttgag caataaagcc gataacaaaa | 3240 |
| tctttgtcgc tcttcgcaat gtcaacagta cccttagtat attctccagt agatagggag | 3300 |
| cccttgcatg acaattctgc taacatcaaa aggcctctag gttcctttgt tacttcttct | 3360 |
| gccgcctgct tcaaaccgct aacaatacct gggcccacca caccgtgtgc attcgtaatg | 3420 |
| tctgcccatt ctgctattct gtatacaccc gcagagtact gcaatttgac tgtattacca | 3480 |
| atgtcagcaa attttctgtc ttcgaagagt aaaaaattgt acttggcgga taatgccttt | 3540 |
| agcggcttaa ctgtgccctc catggaaaaa tcagtcaaga tatccacatg tgttttagt | 3600 |
| aaacaaattt tgggacctaa tgcttcaact aactccagta attccttggt ggtacgaaca | 3660 |
| tccaatgaag cacacaagtt tgtttgcttt tcgtgcatga tattaaatag cttggcagca | 3720 |
| acaggactag gatgagtagc agcacgttcc ttatatgtag cttttcgacat gatttatctt | 3780 |
| cgtttcctgc aggtttttgt tctgtgcagt tgggttaaga atactgggca atttcatgtt | 3840 |
| tcttcaacac tacatatgcg tatatatacc aatctaagtc tgtgctcctt ccttcgttct | 3900 |
| tccttctgtt cggagattac cgaatcaaaa aaatttcaaa gaaaccgaaa tcaaaaaaaa | 3960 |
| gaataaaaaa aaaatgatga attgaattga aaagctgtgg tatggtgcac tctcagtaca | 4020 |
| atctgctctg atgccgcata gttaagccag ccccgacacc cgccaacacc cgctgacgcg | 4080 |
| ccctgacggg cttgtctgct cccggcatcc gcttacagac aagctgtgac cgtctccggg | 4140 |
| agctgcatgt gtcagaggtt ttcaccgtca tcaccgaaac gcgcgagacg aaagggcctc | 4200 |
| gtgatacgcc tatttttata ggttaatgtc atgataataa tggtttctta gtatgatcca | 4260 |
| atatcaaagg aaatgatagc attgaaggat gagactaatc caattgagga gtggcagcat | 4320 |
| atagaacagc taagggtag tgctgaagga agcatacgat accccgcatg gaatgggata | 4380 |
| atatcacagg aggtactaga ctaccttca tcctacataa atagacgcat ataagtacgc | 4440 |
| atttaagcat aaacacgcac tatgccgttc ttctcatgta tatatatata caggcaacac | 4500 |
| gcagatatag gtgcgacgtg aacagtgagc tgtatgtgcg cagctcgcgt tgcattttcg | 4560 |
| gaagcgctcg ttttcggaaa cgctttgaag ttcctattcc gaagttccta ttctctagaa | 4620 |
| agtataggaa cttcagagcg cttttgaaaa ccaaaagcgc tctgaagacg cactttcaaa | 4680 |
| aaaccaaaaa cgcaccggac tgtaacgagc tactaaaata ttgcgaatac cgcttccaca | 4740 |
| aacattgctc aaaagtatct ctttgctata tatctctgtg ctatatccct atataaccta | 4800 |
| cccatccacc tttcgctcct tgaacttgca tctaaactcg acctctacat tttttatgtt | 4860 |
| tatctctagt attactcttt agacaaaaaa attgtagtaa gaactattca tagagtgaat | 4920 |
| cgaaaacaat acgaaaatgt aaacatttcc tatacgtagt atatagagac aaaatagaag | 4980 |
| aaaccgttca taattttctg accaatgaag aatcatcaac gctatcactt tctgttcaca | 5040 |
| aagtatgcgc aatccacatc ggtatagaat ataatcgggg atgcctttat cttgaaaaaa | 5100 |
| tgcacccgca gcttcgctag taatcagtaa acgcgggaag tggagtcagg cttttttat | 5160 |
| ggaagagaaa atagacacca aagtagcctt cttctaacct taacggacct acagtgcaaa | 5220 |
| aagttatcaa gagactgcat tatagagcgc acaaaggaga aaaaagtaa tctaagatgc | 5280 |

```
tttgttagaa aaatagcgct ctcgggatgc attttttgtag aacaaaaaag aagtatagat   5340
tctttgttgg taaaatagcg ctctcgcgtt gcatttctgt tctgtaaaaa tgcagctcag   5400
attctttgtt tgaaaaatta gcgctctcgc gttgcatttt tgttttacaa aaatgaagca   5460
cagattcttc gttggtaaaa tagcgctttc gcgttgcatt tctgttctgt aaaaatgcag   5520
ctcagattct ttgtttgaaa aattagcgct ctcgcgttgc attttttgttc tacaaaatga   5580 agcacagatg cttcgttcag gtggcacttt tcggggaaat gtgcgcggaa cccctatttg   5640 tttattttc taaatacatt caaatatgta tccgctcatg agacaataac cctgataaat   5700
gcttcaataa tattgaaaaa ggaagagtat gagtattcaa catttccgtg tcgcccttat   5760 tcccttttt gcggcatttt gccttcctgt ttttgctcac ccagaaacgc tggtgaaagt   5820
aaaagatgct gaagatcagt tgggtgcacg agtgggttac atcgaactgg atctcaacag   5880
cggtaagatc cttgagagtt ttcgccccga agaacgtttt ccaatgatga gcacttttaa   5940
agttctgcta tgtggcgcgg tattatcccg tattgacgcc gggcaagagc aactcggtcg   6000
ccgcatacac tattctcaga atgacttggt tgagtactca ccagtcacag aaaagcatct   6060 tacgatggg atgacagtaa gagaattatg cagtgctgcc ataaccatga gtgataacac   6120
tgcggccaac ttacttctga caacgatcgg aggaccgaag gagctaaccg cttttttgca   6180
caacatgggg gatcatgtaa ctcgccttga tcgttgggaa ccggagctga atgaagccat   6240
accaaacgac gagcgtgaca ccacgatgcc tgtagcaatg gcaacaacgt tgcgcaaact   6300
attaactggc gaactactta ctctagcttc ccggcaacaa ttaatagact ggatggaggc   6360
ggataaagtt gcaggaccac ttctgcgctc ggcccttccg gctggctggt ttattgctga   6420
taaatctgga gccggtgagc gtgggtctcg cggtatcatt gcagcactgg ggccagatgg   6480
taagccctcc cgtatcgtag ttatctacac gacggggagt caggcaacta tggatgaacg   6540
aaatagacag atcgctgaga taggtgcctc actgattaag cattggtaac tgtcagacca   6600
agtttactca tatatacttt agattgattt aaaacttcat ttttaattta aaaggatcta   6660
ggtgaagatc ctttttgata atctcatgac caaaatccct taacgtgagt tttcgttcca   6720
ctgagcgtca gaccccgtag aaaagatcaa aggatcttct tgagatcctt tttttctgcg   6780
cgtaatctgc tgcttgcaaa caaaaaaacc accgctacca gcggtggttt gtttgccgga   6840
tcaagagcta ccaactcttt ttccgaaggt aactggcttc agcagagcgc agataccaaa   6900
tactgtcctt ctagtgtagc cgtagttagg ccaccacttc aagaactctg tagcaccgcc   6960
tacatacctc gctctgctaa tcctgttacc agtggctgct gccagtggcg ataagtcgtg   7020
tcttaccggg ttggactcaa gacgatagtt accggataag gcgcagcggt cgggctgaac   7080
ggggggttcg tgcacacagc ccagcttgga gcgaacgacc tacaccgaac tgagatacct   7140
acagcgtgag ctatgagaaa gcgccacgct tcccgaaggg agaaaggcgg acaggtatcc   7200 ggtaagcgg agggtcggaa caggagagcg cacgagggag cttccagggg gaaacgcctg   7260
gtatctttat agtcctgtcg ggtttcgcca cctctgactt gagcgtcgat ttttgtgatg   7320
ctcgtcaggg gggcggagcc tatggaaaaa cgccagcaac gcggcctttt tacggttcct   7380
ggccttttgc tggccttttg ctcacatgtt ctttcctgcg ttatcccctg attctgtgga   7440
taaccgtatt accgcctttg agtgagctga taccgctcgc cgcagccgaa cgaccgagcg   7500
cagcgagtca gtgagcgagg aagcggaaga gcgcccaata cgcaaaccgc ctctccccgc   7560
gcgttggccg attcattaat gcagctggca cgacaggttt cccgactgga aagcgggcag   7620
tgagcgcaac gcaattaatg tgagttacct cactcattag gcacccagg ctttacactt   7680
```

```
tatgcttccg gctcctatgt tgtgtggaat tgtgagcgga taacaatttc acacaggaaa    7740
cagctatgac catgattacg ccaagcgcgc aattaaccct cactaaaggg aacaaaagct    7800
ggagctttt                                                            7809
```